US005725487A

United States Patent [19]
Freeman et al.

[11] Patent Number: 5,725,487
[45] Date of Patent: Mar. 10, 1998

[54] ORTHOPEDIC CASTING TAPE

[75] Inventors: Horace L. Freeman, Burlington, N.C.; Richard Green, Livingston, N.J.; James V. Snipes, Clemmons, N.C.

[73] Assignee: Johnson & Johnson Professional, Inc., New Brunswick, N.J.

[21] Appl. No.: 481,912

[22] Filed: Jun. 7, 1995

[51] Int. Cl.⁶ .......................... A61F 13/00; A61F 15/00; A61L 15/00
[52] U.S. Cl. .......................................................... 602/8
[58] Field of Search .............................. 602/1, 6–8, 60, 602/75–77, 900, 41, 44, 45, 47; 66/190, 192, 195, 202

[56] References Cited

U.S. PATENT DOCUMENTS

| | | | |
|---|---|---|---|
| 4,376,438 | 3/1983 | Straube et al. | |
| 4,411,262 | 10/1983 | von Bonin et al. | |
| 4,502,479 | 3/1985 | Garwood et al. | |
| 4,572,171 | 2/1986 | Wegner et al. | |
| 4,668,563 | 5/1987 | Buese et al. | |
| 4,940,047 | 7/1990 | Richter et al. | 602/6 X |
| 4,984,566 | 1/1991 | Sekine et al. | |
| 5,027,804 | 7/1991 | Forsyth et al. | |
| 5,088,484 | 2/1992 | Freeman et al. | |
| 5,403,267 | 4/1995 | Pearce et al. | 602/8 |
| 5,445,599 | 8/1995 | Edenbaum | 602/76 |
| 5,461,885 | 10/1995 | Yokoyama et al. | 66/170 |
| 5,505,692 | 4/1996 | Cho | 602/8 |
| 5,522,241 | 6/1996 | King | 66/193 |
| 5,531,667 | 7/1996 | Webb et al. | 602/8 |

OTHER PUBLICATIONS

"Development of a Water–activated Plastic Cast" by M. J. Lysaght and T. R. Rich (9th Annual International Biomaterials Symposium –1983).

Primary Examiner—Michael Powell Buiz
Assistant Examiner—Chalin Smith
Attorney, Agent, or Firm—Bell Seltzer Intellectual Property Law Group; Alston & Bird LLP

[57] ABSTRACT

The invention is directed to orthopedic casting tapes including an open mesh fibrous tape coated with a hardenable liquid resin, preferably a water activatable resin, that permits shaping and curing of the tape to provide a hardened cast. The fibrous tape is a knit tape is formed primarily or entirely of unbulked, continuous polymeric filaments and elastic filaments. A plurality of continuous filament courses extend generally transverse to the plurality of wales and are present in the fibrous tape in an amount of at least 15 courses per linear inch of tape, measured in a relaxed state. The wales are present in the fibrous tape in an amount sufficient to provide at least about 275 openings per square inch. The casting tape has an extensibility of at least about 5 percent. The orthopedic casting tapes of the invention cure rapidly despite their fine mesh/high mesh content structure and normally are set within 3–5 minutes following application. Hardened casts of five layers formed from the casting tapes of the invention typically have a 24 hour crush strength comparable to or greater than the strength of casts made from fiberglass casting tapes currently used in commerce.

33 Claims, 3 Drawing Sheets

ORTHOPEDIC CASTING TAPE

FIELD OF THE INVENTION

The invention relates to improved orthopedic casting tapes and to orthopedic casts. More specifically, the invention relates to synthetic orthopedic casting materials based on knit synthetic fiber substrates that have strength comparable to or exceeding the strength of conventional synthetic casting materials based on glass fiber substrates.

BACKGROUND OF THE INVENTION

Polymeric or synthetic casting materials have achieved widespread commercial acceptance over the past decade. Synthetic casting materials have various advantages over conventional Plaster of Paris casts in that they are lighter, stronger and, due to the porous nature of the materials used, breathable. Traditionally, orthopedic synthetic casts have been made from a curable resin-impregnated narrow fabric or casting tape formed of glass fibers and/or synthetic fibers such as polyester, nylon, polyolefins and the like.

In the United States, knitted fabrics of continuous filament glass fibers have been the preferred material for forming synthetic cast substrates because of the desire for strength in the fully hardened cast. Although numerous different fabrics based on various types of low modulus synthetic and natural non-glass fibers have been proposed, tested, and/or used commercially to form substrates for synthetic casts, invariably, the strength of these casts have been markedly inferior to the glass substrate casts when compared on a basis including cast thickness and weight. It is thus generally understood in the casting industry that cast strength comparable to that of the conventional five layer, glass fiber-based cast, can only be achieved in a low modulus synthetic fiber-based cast by using more layers of casting tape, an increased basis weight fabric, and/or tapes having an undesirably high fabric thickness. See for example, U.S. Pat. No. 4,502,479 to Garwood et al. which discusses the need for use of high modulus fibers, preferably glass fibers, in order to form casts of adequate strength and rigidity.

As a practical matter, the strength deficiencies of synthetic fiber-based casts significantly decrease patient comfort and/or increase the cost of the final cast. Thus, increasing the number of layers used to form the cast necessitates increasing the time spent by skilled medical personnel in applying the cast to the patient. Likewise, the additional cast layers increase both the fabric and resin content of the cast, thus adding to raw materials and manufacturing costs. When cast weight and/or thickness are increased, the mobility and comfort of the patient are impeded by the increased weight and/or bulk of the cast.

However, despite strength deficiencies and other shortcomings associated with synthetic fiber casts, the medical and orthopedic casting industries have continued to seek synthetic fiber based casting materials which are functionally comparable to glass fiber based casting materials due to a number of different problems associated with glass fibers. For example, glass fibers interfere with the passage of x-rays and thus the glass fiber based casts can impede x-ray monitoring of an immobilized bone, while many synthetic fiber based casts are substantially transparent to x-rays. Similarly, the inherent stiffness of glass fibers, although contributing substantially to improved strength properties in hardened casts, also causes various problems in fabric manufacturing processes such as knitting and thus increases manufacturing costs. The glass fiber stiffness also causes knit fabrics to unravel upon cutting, which in turn necessitates the addition of special processing steps to the conventional fabric manufacturing process.

In recent years, some hospitals have expressed concerns over glass dust which can be generated when a glass fiber based cast is removed, by cutting, from the body. The glass dust is considered by some to be potentially irritating or objectionable to patients or hospital personnel who regularly remove the casts. As a result, many hospitals, particularly in Europe, now prefer to avoid the use of glass fiber based casting tapes altogether. More recently, patterned casting materials have been developed and have gained widespread acceptance and consumer appeal; and although a variety of patterns can readily be applied to casting tapes formed of synthetic and/or glass fibers as disclosed U.S. Pat. No. 5,088,484 to Freeman et al, the inert nature of the glass surface increases the cost associated with the application of a visible pattern to the casting tape.

Because of these and other problems, substantial research and development effort has been directed over a number of years to the development of casting materials free of glass fibers yet having strength and other functional properties comparable to those of a glass fiber casts. One straightforward approach to improving strength of synthetic fiber based casts involves the substitution of high modulus synthetic fibers, such as polyaramide, carbon or similar reinforcing fibers, for the high modulus glass fibers. Although incorporating these materials into the casting tape can achieve substantial strength improvements, the associated costs of such casting tapes are prohibitive.

A different approach for obtaining improved strength in synthetic fiber casting tapes has relied on fabric constructions which are designed to enhance fabric absorbency thereby increasing resin pickup by the fabric. As disclosed in M. J. Lysaght and T. R. Rich; "Development of a Water-activated Plastic Cast"; 9th Annual International Biomaterials Symposium (1983); it is generally understood that the degree of resin impregnation or absorption can be varied between upper and lower practical limits to vary cast strength. In effect, the enhancement of resin pickup allows the resin strength to partially overcome the strength deficiencies of lower modulus synthetic fibers. Accordingly, fabric constructions promoting enhanced resin absorption are found in a variety of commercially available casting materials. Indeed, most commercially available synthetic casting tapes which are not based on glass fibers include textured or otherwise bulked synthetic filaments, and/or wool, cotton or synthetic staple fibers resulting in increased resin pick-up per unit area i.e., per square inch of the tape. The use of bulked and staple synthetic fibers in synthetic casting tapes can be seen throughout the art, for example, in U.S. Pat. No. 4,940,047 to Richter et al., U.S. Pat. No. 4,411,262 to von Bonin et al., U.S. Pat. No. 4,572,11 to Wegner et al. and U.S. Pat. No. 4,984,566 to Sekine.

Other fabric properties are also known to improve cast strength. Notably, mesh size, i.e., the number of holes per square inch of fabric, is believed to have an effect not only on the circulation of air through the hardened cast and evaporation of moisture from beneath the cast, but also on the strength of the hardened casting tape. See, for example U.S. Pat. No. 5,027,804 to Forsyth et al., which discloses fabric constructions having a mesh size of between 120-250 openings per square inch and U.S. Pat. No. 4,502,479 to Garwood et al., which discloses fabrics having a mesh of between 20-200 openings per square inch. In the latter, it is said that when mesh size is too fine, early cast strength is harmed by uneven hardening of the resin and that a high cured cast strength can be unobtainable.

The search for synthetic fiber casting materials comparable to glass based materials involves significant functional requirements beyond considerations of strength. Other important attributes include fabric conformability and extensibility, fabric smoothness, breathability and absorbency. Conformability is important because body surfaces are not uniformly shaped and portions of the casting tape must conform to the body surfaces without causing pressure points. If the casting tape lacks the ability to stretch, it is necessary to form tucks in the cast during application which typically result in a pressure point, causing discomfort to the patient. See, for example U.S. Pat. No. 4,668,563 to Buese et al. which discloses high strength synthetic casts made from conformable knitted glass fiber substrates. Smoothness is considered important because when the cast hardens and becomes rigid, its surface properties are determined in large part by the substrate. If the cast substrate is rough, the resultant cast can have a rasp-like surface which is abrasive on adjacent skin and/or clothing. Absorbency is considered important because, as discussed above, the strength of the ultimate cast is dependent in large part on the pickup of resin by the fabric during manufacture.

The numerous requirements which must be met by any synthetic fiber casting material to provide a functionally comparable substitute for glass based casting materials have limited the available options for overcoming the inherent strength deficiencies of synthetic fibers as compared to glass fibers. Thus, despite years of continued efforts and increasing market demand, as of yet there is no commercially available high strength, synthetic fiber based synthetic casting material.

SUMMARY OF THE INVENTION

The present invention provides synthetic fiber orthopedic casting tapes capable of forming hardened casts having a strength comparable to or exceeding the strength of glass fiber based casts on a normalized basis, i.e., casts formed by tapes of substantially identical width and applied in a like number of layers to form a hardened cast. The synthetic fiber orthopedic casting tapes of the invention also provide functional properties, for example, conformability, breathability, ease of application, and the like, which are comparable to, or exceed functional properties of glass fiber casting tapes widely used in commerce. The synthetic fiber orthopedic casting tapes of the invention are typically smoother and include a higher density of mesh openings as compared to glass-based casting tapes and other synthetic casting tapes currently available and used in commerce. Because of the improved smoothness and a greater number of openings in the casting tape, the casting tape of the present invention is not only stronger but also better suited to provide visibly patterned casting tapes because the visible patterns can be clearer and more defined than with prior art casting tapes.

The orthopedic casting tape of the present invention includes an open mesh fibrous tape coated with a hardenable liquid resin, preferably a water activatable resin, that permits shaping and curing of the tape to provide a hardened cast. The fibrous tape is a knit tape is formed primarily or substantially entirely of unbulked, continuous polymeric filaments and elastic filaments. A plurality of continuous filament wales extend longitudinally along the fibrous tape and at least a portion of the wales include the elastic filaments. A plurality of continuous filament courses extend generally transverse to the plurality of wales and are present in the fibrous tape in an amount of at least 15 courses per linear inch of tape, measured in a relaxed state, and, more preferably, there are between about 17 and about 22 courses per inch of tape. The wales are present in the fibrous tape in an amount sufficient to provide at least about 275 openings per square inch. The casting tape has an extensibility of at least about 5 percent and preferably the extensibility is greater than about 10 to 15 percent due to the elastic filaments which are adjacent or incorporated into the wales under tension during the knitting process. The elastic filaments also pull the courses closely together following the knitting process thereby increasing the mesh count and thickness of the casting tape. Preferably, the continuous filament courses and wales are formed from continuous multifilament polyester textile yarns each having a total denier of about 150 denier or greater.

The orthopedic casting tapes of the invention are believed to provide the first casting tapes based on low modulus synthetic fibers having normalized crush strengths comparable to or exceeding those of glass fiber orthopedic casts without substantially increasing cast thickness and/or weight, and while also providing conformability, breathability, ease of application and cure properties comparable to or exceeding those of glass. The orthopedic casting tapes of the invention cure rapidly despite their fine mesh/high mesh density structure and normally are set within a time of less than 2–5 minutes following application to the patient. The casting tapes of the invention can readily provide 5 layer hardened casts from tapes of 3 inch width having a 24 hour crush strength exceeding premium fiberglass cast strengths of 85 pounds with minimal or no substantial increase in weight of the cast, and without sacrifice of other functional properties such as conformability, breathability, ease of application, and the like. Hardened casts of five layers formed from the casting tapes of the invention typically have a 24 hour crush strength of greater than 20, and more typically greater than about 22–23 pounds per inch width of the casting tape, although lower strength casting tapes according to the invention can find advantageous use in less demanding applications. Preferred casting tapes of the invention can provide five layer casts having a 24 hour crush strength in the range about 25 pounds per inch width of casting tape, up to and even exceeding 50 pounds per inch width of casting tape, i.e., more than double the strength of casts made from premium grade fiberglass casting tapes currently used in commerce.

Although the mechanism or mechanisms responsible for the improved strength in the casting materials of the invention are not fully understood, and while the inventors do not wish to be bound by any particular theory, it is presently believed that the arrangement of the courses, wales, and the increased number of openings and thickness in the fabric cooperate to provide increased strength benefits from the resin absorbed onto or into the casting tape, and from the continuous filament fibers used to form the tape. The elastic filaments present in the wales, which contract the tape along its length direction and thicken the tape in the "Z" direction, clearly function to improve the strength of the hardened plastic cast. The improved smoothness of the tape, the decreased yarn-to-yarn distance in the final knit casting tape, and the thickened, three-dimensional structure of the fabric are believed to allow the resin to achieve a greater degree of yarn-to-yarn and layer-to-layer bonding in the final cast as opposed to a more inefficient use of the resin strength to achieve enhanced bonding within each multifilament yarn forming the courses and wales.

Although various different continuous filament synthetic fibers can be used to form the casting tapes of the invention, preferably the tapes are formed substantially entirely of textile grade polyethylene terephthalate yarns in combination with mono- or multi-filament continuous elastomeric yarns. Preferred elastomeric yarns include wrapped and unwrapped yarns based on natural or synthetic rubber or rubber-like elastomers including dynamically vulcanized, blended polypropylene and EDPM, commercially available as Santoprene®, silicone elastomers, or thermoplastic elastomers such as styrene(ethylene-butylene)styrene block copolymers and the like. The elastic yarns are preferably included in at least about one fourth, preferably at least about one third of the wales and are preferably distributed across the width of the fabric substantially evenly, e.g., every fourth wale, every third wale, every other wale, or every wale. In addition to improving the strength and the smoothness of the final casts, the elastic yarns also improve the conformability and ease of application of the casting tapes. In addition, the closeness or optical density of the fabric improves its ability to receive and display visible patterns.

Advantageously, the elastomeric filamentary material is substantially inert to the liquid resin to enable the casting tape to have both the desired extensibility prior to curing of the liquid resin, and have a greatly increased shelf life. Preferably the liquid resin is a polyurethane prepolymer. Advantageously the casting tape is provided in a sealed, water-tight package.

BRIEF DESCRIPTION OF THE DRAWINGS

In the drawings which form a portion of the original disclosure of the invention.

DETAILED DESCRIPTION OF THE PREFERRED EMBODIMENTS

In the following detailed description, preferred embodiments are discussed in detail to enable practice of the invention. It will be apparent that although specific terms are used to describe the preferred embodiments, these are used in the descriptive sense and not for the purpose of limiting the invention thereto. It will also be apparent that the invention is susceptible to numerous changes and may be embodied in many different forms other than the preferred embodiments specifically described below as will become apparent from a consideration of the invention as shown in the attached drawings and described below. In the drawings, like numbers refer to like elements throughout.

Figure 1:
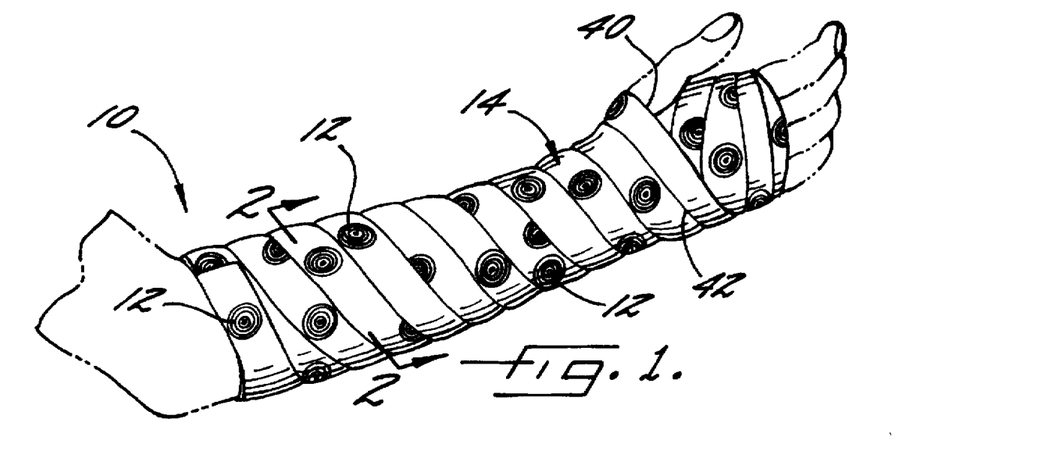
FIG. 1 is a side view in perspective illustrating a synthetic cast made from a preferred casting tape in accordance with the present invention.

FIG. 1 illustrates an orthopaedic cast 10 according to the invention. The cast 10 advantageously includes visible patterned areas 12 which, although optional, can significantly enhance the patient's mental comfort. The visible patterned areas 12 are provided by one or more coloring agents visibly disposed on the fibrous tape 14.

Figure 2:
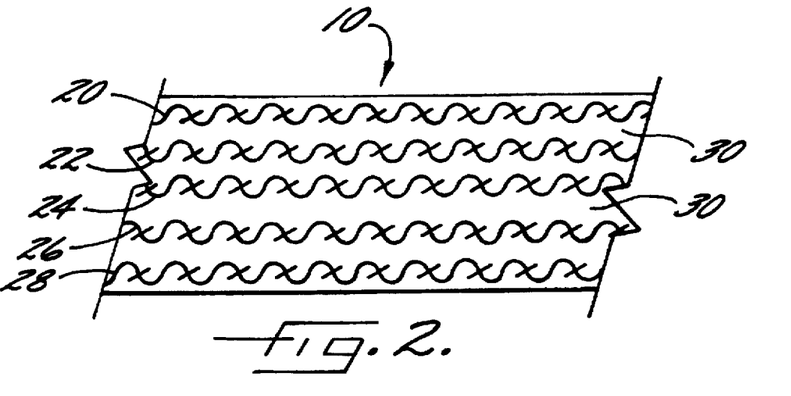
FIG. 2 is a schematic representation of a greatly enlarged, partial cross-sectional view of the cast of FIG. 1 taken along line 2—2 thereof and illustrates the layered structure of casts according to the invention.

As illustrated in FIG. 2, the cast of FIG. 1 is typically composed of a plurality of layers 20, 22, 24, 26, and 28. It will be apparent to the skilled artisan that although five cast layers are illustrated in FIG. 2, a typical orthopedic cast can be composed of greater or fewer numbers of layers depending upon various considerations and strength requirements. However a five layer cast is commonly considered advantageous due to considerations of breathability and weight.

Intimately surrounding each of layers 20–28 is a hardened polymer matrix material 30. Although not shown in FIG. 2, because fibrous layers 20–28 are porous, the resultant cast 10 is likewise porous and breathable; thus, there are numerous openings in the hardened polymer matrix 30 throughout the hardened cast 10.

Figure 3:
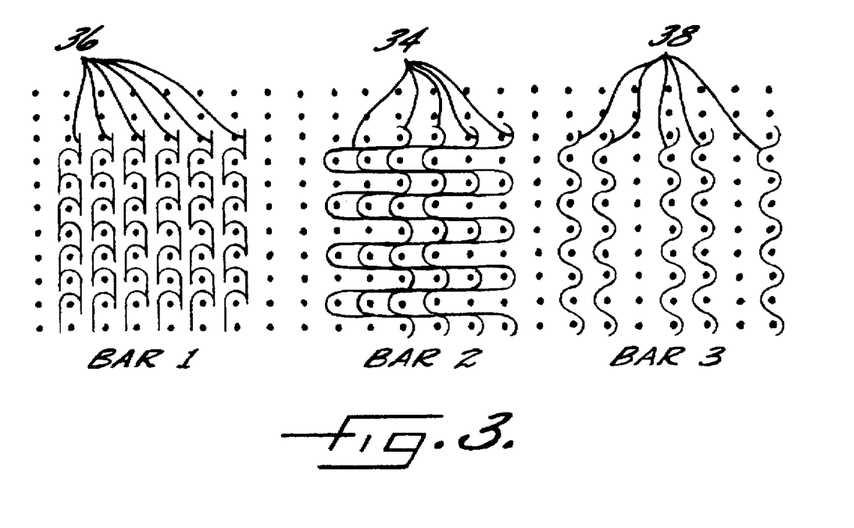
FIG. 3 is a diagram illustrating the knit notation for one preferred tape embodiment of the invention comprising a three bar Raschel knit in which bar 1 forms simple chain stitch wales, bar 2 preforms a lapping motion to lay in yarns forming the courses in the knit fabric, and bar 3 lays in elastic filaments in every second and third wale for each set of three wales transversely across the fabric.
Figure 4:
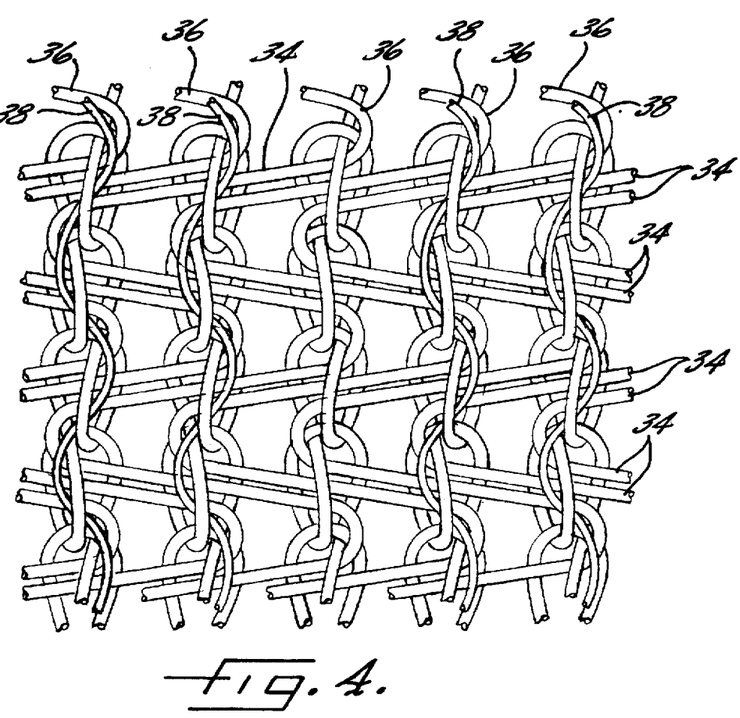
FIG. 4 illustrates a greatly enlarged perspective view of a portion of the knit fabric structure formed in accordance with the knit notation of FIG. 3 in which wales and the elastic filaments therein are shown in conditions of stretch to better illustrate the fabric structure.
Figure 6:
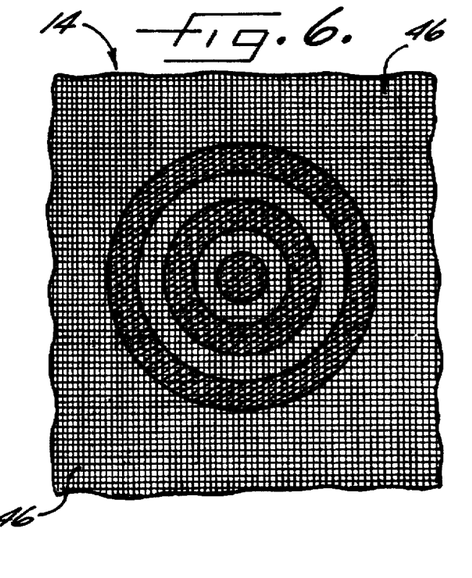
FIG. 6 is a top plan view illustrative of a visibly patterned casting tape of the invention and illustrates the improved optical density and clarity of a printed pattern as it appears thereon.

As illustrated in FIGS. 3, 4 and 6, the open mesh fibrous casting tape 14, of the invention includes a knit fabric structure defined by a plurality of courses 34 and wales 36. The wales 36 extend longitudinally along the casting tape and the courses 34 extend generally transverse to the wales 36, i.e., the courses 34 extend in the width direction of the casting tape. The courses 34 and wales 36 are advantageously made from synthetic multifilament continuous yarns having a low affinity for moisture including yarns made from polyesters, preferably polyethylene terephthalate, or polyolefins, preferably polypropylene. The courses 34 and wales 36 can also be formed from synthetic multifilament continuous yarns having a greater affinity for moisture such as polyamides including nylon 6 and nylon 6,6, and acrylics, acetates and the like. Moisture absorbing yarns can complicate the polymer coating process when the preferred water activatable polymers are employed and can interfere with the shelf life of the preferred packaged product and are not preferred for this reason. Polyethylene terephthalate continuous yarns are presently preferred for forming courses 34 and wales 36.

Although both textile and industrial grade continuous yarns can be used to form the courses 34 and wales 36, advantageously, the continuous yarns are of textile grade intrinsic viscosity and tenacity, i.e., having a tenacity of less than about 8 grams per denier, preferably less than about 7 grams per denier, which increases the conformability and smoothness of the final casting tape. Surprisingly, such textile grade continuous yarns having total deniers as low as 150 denier can be used to form both courses and wales and yet provide final hardened casts of five layers having a crush strength exceeding about 15 pounds, preferably exceeding about 20 pounds per inch of tape width, e.g., a crush strength of 60 lbs for a 3 inch width tape or greater. Unless otherwise noted, as used throughout the present application, the term "crush strength" is used to mean crush strength measured on a standard compression testing apparatus oriented to apply an increasing compression load to opposed circumferential surfaces of a cylindrical test specimen in a direction transverse to the longitudinal axis thereof, measured in pounds load required to achieve a 1 cm. deflection of a 24 hour-cured, 2.75 inch inside diameter, approximately 3 inch cylinder length, test specimen.

The continuous multifilament yarns are flat yarns, i.e., substantially free of texturing or other processing for substantially increasing bulk. It is preferred that the yarns also be free of any substantial amount of twist although air jet "tacking" and/or the inclusion of some small degree of twist simply to maintain yarn integrity is normal. It is also preferred that total denier of the yarns used to form the courses and wales 34 and 36 be less than about 500 denier in order to enhance smoothness and uniformity in the final casting tapes of the invention.

A portion, or all of the wales 36 include an elastic extensible yarn 38. Preferably the elastic yarn is formed of an elastomeric material, i.e., a fiber forming material which provides an inherent stretch and recovery. The elastic extensible yarn can be formed of an acid treated natural rubber or a synthetic thermoplastic elastomer such as polyisoprene, polybutadiene, styrene-diene copolymers including di- and tri-block copolymers of styrene with butadiene, isoprene, or saturated or unsaturated ethylene-propylene copolymer blocks such as the KRATON™ elastomers, copolymers of acrylonitrile and a diene, polychloroprene, copolymers of polychloroprene and other monomers, ethylene-propylene thermoplastic elastomers including ethylene-propylene copolymers and ethylene-propylene-diene terpolymer elastomers and block copolymers of ethylene and butene, hexene, octene, decene, or 4-methylpentene, commercially available as Exact™ resins, polyester-polyether elastomers commercially available as Hytrel™ resins, polyurethanes, elastomers based on polyurethanes and polyethers including materials commercially available as Pellathane™, silicone elastomers including high molecular weight linear divinyl polydimethylsiloxanes and silicone hydride cross-linked polymers thereof, polyether-polyamide elastomers available as Pebax™, and the like.

Yarns formed of a dynamically vulcanized blend of olefin rubber and thermoplastic olefin resin, such as those disclosed in U.S. Pat. No. 4,130,535, and preferably a dynamically vulcanized blend of polypropylene and EDPM rubber, commercially available as Santoprene®, are currently preferred because it has been found that these yarns are substantially inert to water-activatable resins so as to provide the casting tape with a shelf life of between two and four years, while maintaining a recoverable elongation of about 70%.

The elastic yarns 38 are preferably included in at least about one fourth, preferably at least about one third of the wales and are preferably distributed across the width of the fabric substantially uniformly, e.g., every fourth or every third wale, every other wale, or every wale, etc. More preferably, the elastic yarns 38 are included in at least about one half of the wales and are distributed across the width of the fabric substantially uniformly.

As illustrated, the casting tape fabric 14 is a knit, open mesh fabric preferably including selvage edges 40 and 42 (FIG. 1) on the opposed transverse edges thereof. The open mesh fibrous tape 14 includes mesh openings 46 (FIG. 6) throughout the structure of the fabric which allow full and complete penetration of the hardenable liquid polymer into the fabric and provide porosity in the hardened cast.

The quantity of mesh openings 46 is unusually high in the casting tapes 14 of the invention. Advantageously the number of mesh openings 46 in the casting tapes of the invention will exceed about 275 openings per square inch. For the purposes of this application, the mesh opening number is determined on a surface area basis by multiplying the courses per unit of measured length of casting tape, times the number of wales per unit of measured width of casting tape, wherein the casting tape length and width is measured while the tape is maintained in a relaxed state and prior to coating with resin. Preferably the number of mesh openings 46 in the casting tapes of the invention will exceed about 300 openings per square inch, and more preferably will exceed about 325 to about 350 openings per square inch.

The casting tape has an extensibility of at least about 5 percent and preferably the extensibility is greater than about 10 to 15 percent due to the elastic filaments which are associated with or incorporated into the wales under tension during the knitting process. The elastic filaments also pull the courses closely together following the knitting process thereby increasing the mesh count and thickness of the casting tape. Preferably, the continuous filament courses and wales are formed from continuous multifilament polyester textile yarns each having a total denier of about 150 denier or greater.

The orthopedic casting tape 14 of the invention can be knit on various and numerous knitting apparatus. However, it is preferred that a Raschel Warp Knitting apparatus be employed. FIGS. 3 and 4 illustrate one preferred warp knit construction for the casting tape 14 of the invention. Preferably, the knitting machine should exceed about 10–12 needles per inch depending on yarn denier and the number of courses per inch, and more preferably, should include from about 14 to about 28 needles per inch, for example, about 18 needles per inch. In practice, the knit fabric will typically contract substantially both along its length (machine direction) and across its width (cross-machine direction) due to the inclusion of elastic yarns some or all of the wales. In the finished state, the casting tapes are typically provided in widths ranging from about two inches (5 centimeters) to about 5 inches (about 13 centimeters); however during the knitting process, the knit tape will normally have a greater width and increased length.

The knitting process is conducted provide uniform and closely spaced continuous filament courses in an amount of at least about 15 courses per linear inch of tape, measured in a relaxed state. Preferably, there are at least about 16 courses per linear inch of tape, more preferably, there are between about 17 and about 22 courses per inch of tape. The wales are provided in the in the fibrous tape in an amount sufficient, based on the number of courses, to provide at least about 275 openings per square inch. The number of courses and wales can be varied depending on factors such as yarn denier and strength, and also depending on the fabric weight, smoothness, strength, and number of mesh openings desired in the final orthopedic casting tape.

FIGS. 3 and 4 illustrate one preferred warp knit construction for casting tapes of the invention. FIG. 3 shows graphically the knit notation for the three bars on the three bar Rachel warp knitting machine used to provide the fabric structure of FIG. 4. Bar 1 uses a stitch notation of 2 0 0 2 to provide a simple chain stitch thereby forming a plurality of wales 36, as shown in FIG. 4. Bar 2 uses a knit notation of 0 0 6 6 and forms a lapping motion to provide laid in course yarns of FIG. 4. Each of bars 1 and 2 use one end (yarn) per needle. Bar 3 uses a knit notation of 2 2 0 0 and also forms a lapping motion to provide laid in course yarns 36 of FIG. 4. Bar 3 uses one end for each needle. As a result of the motion of bar 3, two of each set of three wales 36 include a laid in elastomeric yarn 38 from bar 3. As indicated previously, elastic yarns 38 can be laid into all of the wales 36 or can be lain into less than the 66% of the wales 36 as shown in FIGS. 3 and 4.

As will be apparent to those of skill in the art the structure and knit notations for forming casting tapes according to the invention can be widely varied. For example the lapping motion of bar 2 can be greater or less than shown in FIG. 3. Similarly, elastomeric yarns can be laid in by bar 3 in a wide variety of lapping motions and varying patterns, for example using the knit notation 2 2 4 4 2 2 0 0. In this case, bar 3 lays in yarns on two adjacent needles for each set of four needles.

The orthopedic casting tapes 14 of the invention have an extensibility of at least about 5%, preferably at least about 10%, more preferably at least about 15% and even more preferably at least about 20%. Extensibility is measured by applying a weight of 1.5 lbs. per inch width of the casting tape to a sample of the uncoated casting tape, i.e., knit fabric, which has a length of 10 inches for a time sufficient that elongation is substantially unchanging. Extensibility is calculated by expressing the increase in length as a percentage of the original tape length, wherein the term extensibility, as used herein, applies to elongations which are at least about 60%, preferably at least about 70%, recoverable when the weight is removed within a short time following stabilization of elongation. It is also preferred that the extensibility of the tape be maintained to an amount less than about 100% since high extensibilities can promote uneven, corrugated-like gathering in the tapes of the invention due to their construction from continuous filaments lacking the stiffness of glass fibers. In highly preferred embodiments of the invention, the tape has an extensibility prior to coating, in the range of about 40% to about 85%, and even more preferably, the extensibility is in the range of about 60% to about 70%. As disclosed in U.S. Pat. No. 4,668,563 to Buese et. al., which is hereby incorporated by reference, the power (retractive) of an orthopedic casting bandage is also important. The power should be low to prevent constriction of the patient's limb after the tape is applied to the patient and should be maintained within the range of below 175 grams per inch width based on a fabric stretch of 30%.

The extensibility characteristics of the fabric can be controlled by selection of the type of yarn, the number of elastic filaments and the denier of the filaments as well as the tension on the elastic filaments during knitting. Preferably, the elastic yarns are maintained under a small degree of tension during knitting so that following knitting, when the tension is removed, the elastic yarns retract causing the fabric to contract or becomes compressed along its length and thickened in the "Z" direction. Accordingly, the casting tape 14 tends to assume a thicker, relatively uniform three-dimensional matrix-like structure, thereby increasing the number of mesh openings (on a surface area unit basis) and the depth of the individual mesh openings.

Preferably, the casting tapes of the invention have a smooth surface that is substantially uniform along the length and across the width of the tape. The preferred substantially uniform distribution of the elastic yarns across the width of the fabric enhances the smoothness of the fabric and eliminates or minimizes any uneven corrugated-like "gathering" of the fabric which is to be avoided in preferred embodiments of the invention. Uniformity is also enhanced by choosing substantially identical denier yarns for the wales, and by maintaining substantially uniform tension on the elastic yarns. Preferably the yarns used to form the courses are also of substantially identical denier to each other and also have a denier the same or within about 150 denier of the yarns forming the wales.

In the final orthopedic products of the invention, the generally uniform, three dimensional structure in the fabrics appears to provide a generally evenly distributed network of continuous filaments extending in virtually all directions, including lengthwise along the fabric, transversely across the fabric, and also in the "Z" direction, into and out of the general plane of the fabric. The thickness of the synthetic filament orthopedic casting fabrics of the invention is generally similar to the thickness of prior art glass fiber fabrics. However, unlike conventional prior art synthetic fiber-based, casting tape fabrics which achieve increased thickness by relying on bulked or staple yarns, thickness is achieved in the synthetic filament, orthopedic casting fabrics of the invention by closely spacing the courses and wales and by use of the elastic yarns to force the wales to assume an alternating upwardly and downwardly directed, wave-like configuration which repeats periodically along the length of the fabric.

Figure 5:
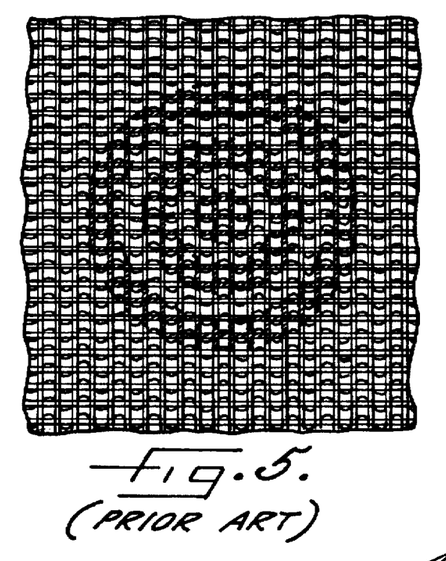
FIG. 5 is a top plan view illustrative of a prior art visibly patterned casting tape and illustrates the optical density of a printed pattern as it appears thereon.

FIGS. 5 and 6 illustrate improved visible patterns that can be realized with the smoother, denser orthopedic tapes of the invention. The prior art visibly patterned casting tape illustrated in FIG. 5 is typical of prior art synthetic fiber casting tapes having a minimal thickness and large individual mesh openings. The optical density and edge definition in similar patterns when applied to the smoother, denser casting tapes of the invention can be greatly improved as illustrated in FIGS. 5 and 6. A wide variety of visible patterns which are stable in the presence of uncured, hardenable casting resins, and also in the presence of the cured, hardened resin, can readily be applied to casting tapes of the invention by a variety of dyeing, sublimination dye printing, or ink printing and like processes disclosed U.S. Pat. No. 5,088,484 to Freeman et al which is incorporated herein by reference. A conventional offset printing process is a presently preferred process for applying visible patterns to casting tapes of the invention. Any of various conventional inks based on various mixtures of a hardenable resin and a pigment can be used to apply the pattern to the fabric tape prior to coating with the hardenable resin, including inks based on air curable resins such as vegetable oils, for example linseed oils, alone or in combination with phenolic resins, or inks based on various synthetic uv-curable resins, heat-curable resins, etc.

Following construction of the casting tape, the tape is coated with a hardenable liquid resin capable of curing to form a hardened plastic. Preferably, the hardenable liquid resin is a water activatable polyurethane prepolymer which is applied in a dry atmosphere to the fabric by a reverse roll coating or other coating technique known to form cast bandages. The weight of the prepolymer is typically within the range of between about 60 and about 400 grams per square meter, preferably between about 80 and 300 grams per square meter to thereby provide a preferred prepolymer weight between about 30% and 70% by weight, based on the total weight of uncoated tape and resin. Preferred water curable polyurethane prepolymers for use in this invention are disclosed in Yoon, U.S. Pat. No. 4,433,680, which is hereby incorporated herein by reference. Immediately after the prepolymer is applied to the fabric, the coated fabric is preferably packaged in a sealed single use or resealable moisture resistant package, preferably in an inert atmosphere to prevent any contact with atmospheric moisture.

Casts formed from the orthopedic casting tapes of the invention have been found to typically have a greater crush strength and impact resistance based on fabric weight, as compared to prior art synthetic fiber casting tapes. This result is not fully understood and may be due to different factors. As indicated previously, the casting tapes of the present invention have been found capable of forming exceptionally strong, hardened structural casts even when the mesh size is greatly outside of the range identified by the prior art as providing strong casting materials. In this regard, U.S. Pat. No. 4,502,479 to Garwood et al. is directed to casting tapes prepared from high modulus fibers and having a mesh size of between 20 and 200 openings per square inch in order to provide finished casts of high breathability and improved strength. The inventors of the present application have found that casts prepared from tapes according to this invention having mesh size openings substantially in excess of 275 openings per square inch have a high degree of strength (both crush and impact) and breathability despite the teachings of the prior art. Thus in advantageous embodiments of the invention, the tapes have openings in excess of 275 per square inch, and even in excess of 350 openings per square inch.

Orthopedic casting tapes according to the invention are capable of forming five layer casts having highly desirable strength to weight ratios expressed in (i) crush strength as the load in pounds required to achieve a 1 cm. deflection of a 24 hour-cured, five layer, 2.75 inch inside diameter, approximately 3 inch cylinder length test specimen; relative to, (ii) the weight of the same 24 hour cured test specimen in grams. Preferred orthopedic casting tapes of the invention are capable of forming five layer casts having strength to weight ratios of at least about 1.25 to 1; more preferably at least about 1.4 to 1; and even more preferably, about 1.5 to 1 or greater. Quite surprisingly, casting tapes of the invention can readily be constructed to achieve strength to weight ratios of about 2 to 1 and higher, and even up to and exceeding 2.5 to 1.

The orthopedic casting tapes of the invention are believed to provide the first casting tapes based on low modulus synthetic fibers which have normalized crush strengths comparable to or exceeding those of glass fiber orthopedic casts without substantially increasing cast thickness and or weight, and while also providing conformability, breathability, ease of application and cure properties comparable to or exceeding those of glass. The casting tapes of the invention readily form casts which set and cure rapidly despite their fine mesh/high mesh content structure. Hardened casts of five layers formed from the casting tapes of the invention advantageously have a 24 hour crush strength of greater than about 15 lbs., and preferably greater than about 20 pounds, more preferably greater than about 22–23 pounds per inch width of the casting tape, while highly preferred casting tapes of the invention provide five layer casts having a 24 hour crush strength of greater than about 25 pounds per inch width of casting tape. Typically the 1 hour crush strength of the casts is about 85–90% of the 24 hour crush strength. The casting tapes of the invention can readily provide 5 layer hardened casts from tapes of 3 inch width having a 24 hour crush strength of about 85 pounds or greater, which is comparable to or greater than the strength of casts made from premium grade fiberglass casting tapes currently in widespread use throughout commerce.

The orthopedic casting tapes of the invention can also exhibit impact strength properties which compare favorably to those prepared from glass fabric casting tapes. The impact strength can be important in addition to the crush strength particularly in applications such as walking casts where the cast is expected to receive repeated impacts. It has also been found that the bending index of casts prepared from the orthopedic casting tapes of the invention exceeds that of casts prepared from glass fabric casting tapes. Bending Index is generally determined by determining the amount of deflection that a 10 inch portion of flat slab of hardened cast material undergoes when this portion of the slab is extended beyond the edge of a support and a predetermined load is applied to the free end of the 10 inch section. Casts having an improved bending index are believed by some physicians to increase the rate of bone healing since minor mechanical stresses can be transmitted to the injured bone and surrounding tissue and promote blood circulation.

The orthopedic casting tapes of the invention can also be used to prepare orthopedic splints and similar orthopedic support materials. Splints are traditionally formed by using a multiple layer, e.g., 5–8 layers, elongate thickened sheet of resin coated casting fabric which is shaped, cured and then used to support an injured area.

EXAMPLE 1

The fabrics of this Example were knitted on a Raschel Warp Knitting Machine using unbulked continuous multifilament polyester yarns, identified below, for bars 1 and 2. Bar 3 was used to supply Santoprene® or rubber elastic filaments (when present in the samples). The fabric constructions were varied to compare fabric having an elastomeric yarn for every wale with fabrics having an elastomeric yarn for only some wales. In addition, the fabric constructions were varied to compare the effect yarn denier and of the overall fabric weight on the characteristics of the resultant cast. In each of the fabrics set forth below, the stitch employed on bar 1 was 2 0 0 2, Bar 2 was 0 0 6 6, and Bar 3, in each case, used the stitch notation, 2 2 0 0.

Casting tapes were made from the fabric tapes by coating with a polyurethane prepolymer to provide a coating weight of approximately 40–60%. The fabrics were weighed prior to and after coating with prepolymer. Cast properties of the samples were determined by exposing the tapes to water and then wrapping a sample having approximately a 3 inch width around a metal dowel having a diameter of 2.75 in. The length of the sample was the length required to prepare a five layer sample or an eight layer sample, as appropriate. Set time was determined by a fingernail indentation test wherein when the resin could no longer be indented by application fingernail pressure the cast was considered set. The resultant cast samples were then allowed to age for 24 hours, at which time crush strength was measured. Crush strength was determined using a Chatilion compression tester. The samples were deflected 1 cm. and the load needed to deflect the cylinders determined. This is reported as crush strength.

The construction and properties of the fabric tapes prior to coating with resin are set forth in Table 1, below. Properties of resin coated tapes and casts made therefrom are set forth in Table 2, below.

In all cases the casting tapes of the invention were easy to apply and had good comformability and breathability. As can be seen in Table 2, the orthopedic casting tapes of the invention cured rapidly despite their fine mesh/high mesh content structure and were are set in less than 3 minutes following application of water. As can also be seen from Table 2, the crush strength of the five layer casts made from samples of the invention are unexpectedly superior to prior synthetic fiber casts since they compare favorably to or exceed casts made from glass fibers. In general, the casting tapes of the invention had 24 hour crush strengths about the same or exceeding the 20–25 lb per inch tape width crush strength exhibited by typical commercial glass fiber orthopedic casts of five layers. In many cases the casting tapes of the invention had 24 hour crush strengths greatly exceeding the 28–29 lb per inch tape width crush strength exhibited by premium commercial glass fiber orthopedic casts of five layers. The remarkable benefits and advantages of the orthopedic casting tape structures of the invention are particularly apparent in the latter, especially since in two samples, the crush strength exceeded by over 100% the crush strength available from the premium commercial glass fiber orthopedic casts of five layers.

It can be seen from Table 2 below that the casts of the invention had a significantly greater crush strength per unit weight of fabric (coated) than comparable fabrics having a plurality of wales of identical thickness. The casts of the invention had a crush strength which exceeded 20 lbs. per inch tape width in every case except for sample K1-027-5B which included a low denier yarn forming the fabric wales in Combination with a much higher denier yarn forming the fabric courses; however the eight layer crush strength of this sample greatly exceeded that of comparative sample K2-46-2, which had a similar construction but with a significantly larger size of individual mesh openings.

The effect of elastic fibers is apparent from sample K11-309-4 which had a construction identical or comparable to many of the samples of the invention except that sample K11-309-4 included no elastic yarns and consequently the final courses per inch was much lower. Thus the eight layer crush strength of sample K11-309-4 is less than ½ of the crush strength of every sample of the invention except for sample K1-0275B.

TABLE 1

| SAMPLE | TAPE WIDTH | YARN BAR 1* | YARN BAR 2* | YARN BAR 3 | NO. WALES | NO. ELASTIC WALES | COURSES PER INCH RELAXED | PERCENT EXTENS. | NO. OF OPENINGS** |
|---|---|---|---|---|---|---|---|---|---|
| K2-046-2 COMPARATIVE | 3.0 | 1/150 TXT[+] | 1/500 | 95 GG[++] | 33 | 33 | 20.9 | 83.0 | 229.9 |
| K11-309-4 COMPARATIVE | 3.5 | 1/300 | 1/300 | NONE | 72 | 0 | 12.2 | 5.63 | 251 |
| K12-344-4 COMPARATIVE | 3.38 | 1/150 TXT | 1/500 | SANT.[+++] | 33 | 33 | 20.0 | 77.5 | 195.9 |
| K11-312-4 | 3.84 | 1/300 | 1/300 | SANT. | 45 | 45 | 23.33 | 88.13 | 273.4 |
| K12-342-4 | 3.0 | 1/300 | 1/300 | SANT. | 60 | 40 | 16.5 | 52.0 | 330.0 |
| K12-343-4 | 3.18 | 1/300 | 1/300 | SANT. | 64 | 32 | 15.7 | 46.0 | 310.9 |
| K2-048-5A | 3.29 | 1/200 | 1/200 | SANT. | 72 | 72 | 19.0 | 79.67 | 376.4 |
| K2-048-5B | 3.25 | 1/200 | 1/200 | SANT. | 72 | 72 | 19.3 | 75.62 | 409.1 |
| K3-072-5A | 3.46 | 1/300 | 1/300 | SANT. | 64 | 32 | 19.0 | 59.78 | 342.2 |
| K3-072-5B | 3.38 | 1/300 | 1/300 | SANT. | 64 | 32 | 18.5 | 63.25 | 334.6 |
| K3-076-5A | 3.29 | 1/300 | 1/500 | SANT. | 64 | 32 | 18.7 | 98.53 | 363.2 |
| K3-076-5B | 3.33 | 1/300 | 1/500 | SANT. | 64 | 32 | 18.0 | 93.95 | 345.9 |
| K3-068-5A | 3.50 | 1/300 | 1/300 | SANT. | 64 | 32 | 18.0 | 51.43 | 329.1 |
| K3-068-5B | 3.25 | 1/300 | 1/300 | SANT. | 64 | 32 | 17.0 | 51.87 | 334.8 |
| K3-077-5A | 3.27 | 1/200 | 1/300 | SANT. | 72 | 72 | 18.22 | 79.27 | 418.3 |
| K3-077-5B | 3.25 | 1/200 | 1/300 | SANT. | 72 | 72 | 19.0 | 78.10 | 435.8 |
| K1-007-5A | 3.23 | 1/300 | 1/300 | SANT. | 74 | 74 | 18.3 | 65.62 | 419.9 |
| K1-007-5B | 3.19 | 1/300 | 1/300 | SANT. | 74 | 74 | 19.0 | 62.17 | 440.7 |
| K3-073-5A | 2.96 | 1/300 | 1/300 | SANT. | 64 | 64 | 20.0 | 82.5 | 432.4 |
| K3-073-5B | 2.91 | 1/300 | 1/300 | SANT. | 64 | 64 | 20.5 | 79.68 | 450.8 |
| K4-091-5A | 3.50 | 1/300 | 1/300 | SANT. | 64 | 32 | 19.7 | 86.65 | 359.6 |
| K4-091-5B | 3.47 | 1/300 | 1/300 | SANT. | 64 | 32 | 19.0 | 79.05 | 372.1 |
| K3-048-5A | 3.44 | 1/300 | 1/300 | RUBBER | 64 | 32 | 20.0 | 112.28 | 368.8 |
| K3-047-5A | 2.94 | 1/300 | 1/300 | RUBBER | 64 | 64 | 21.0 | 90.20 | 457.1 |
| K1-027-5B | 3.08 | 1/150 | 1/300 | SANT. | 64 | 64 | 21.3 | 67.68 | 443.2 |

*No Ends/Denier
**PER SQUARE INCH
[+]Textured
[++]95 Gauge Natural Rubber
[+++]Santoprene ™
*A = Unprinted
**B = Printed

TABLE 2

| Sample | 24 hr. Crush 5 Layer | 24 hr. Crush 8 Layer | Set Time | Working Time | Fabric Wt. | Resin Wt. | Resin g/sq in | % exten. Coated tape |
|---|---|---|---|---|---|---|---|---|
| K2-046-2 Comparative | N/A | 81 | 3.10 | 2.2 | 37.60 | 57.10 | 0.182 | 64.2 |
| K11-309-4 Comparative | N/A | 126 | N/A | N/A | 59.36 | 72.60 | 0.123 | 5 |
| K12-344-4 Comparative | N/A | 119 | 2.11 | 3.31 | 55.79 | 62.0 | .0223 | 70 |
| K11-312-4 | 88 | 350 | N/A | N/A | 60.13 | 73.50 | 0.109 | 25 |
| K12-342-4 | 38.5 | 113 | 2.91 | 2.22 | 64.20 | 73.60 | 0.199 | 43.2 |
| K12-343-4 | 40.2 | 109 | 2.86 | 2.07 | 65.30 | 69.60 | 0.172 | 34.9 |
| K2-048-5A | 84.1 | 266.1 | 2.78 | 2.00 | 59.37 | 77.56 | 0.204 | 73.5 |
| K2-048-5B | 95.1 | 301.1 | 2.85 | 1.95 | 60.08 | 78.99 | 0.238 | 66.4 |

TABLE 2-continued

| Sample | 24 hr. Crush 5 Layer | 24 hr. Crush 8 Layer | Set Time | Working Time | Fabric Wt. | Resin Wt. | Resin g/sq in | % exten. Coated tape |
|---|---|---|---|---|---|---|---|---|
| K3-072-5A | 86.1 | 253.1 | 2.83 | 2.00 | 59.55 | 77.69 | 0.205 | 40.0 |
| K3-072-5B | 98.1 | 271.1 | 2.88 | 2.09 | 59.40 | 79.65 | 0.214 | 38.8 |
| K3-076-5A | 96.1 | 277.1 | 2.82 | 2.05 | 64.63 | 86.15 | 0.236 | 55.0 |
| K3-076-5B | 112.1 | 282.1 | 2.82 | 2.10 | 65.21 | 84.36 | 0.232 | 48.8 |
| K3-068-5A | 141.1 | 387.1 | 2.95 | 2.05 | 89.20 | 117.36 | 0.267 | 18.8 |
| K3-068-5B | 152.1 | 429.1 | 2.88 | 2.15 | 88.98 | 119.19 | 0.279 | 22.9 |
| K3-077-5A | 108.1 | 319.1 | 2.96 | 2.15 | 67.13 | 88.25 | 0.262 | 67.5 |
| K3-077-5B | 100.1 | 300.1 | 2.85 | 2.05 | 67.06 | 92.07 | 0.257 | 60.4 |
| K1-007-5A | 172.1 | 485.1 | 2.85 | 2.05 | 82.95 | 110.67 | 0.311 | 53.8 |
| K1-007-5B | 144.1 | 398.1 | 2.80 | 2.12 | 83.44 | 107.86 | 0.286 | 44.4 |
| K3-073-5A | 149.1 | 424.1 | 2.80 | 2.05 | 71.04 | 92.68 | 0.305 | 66.0 |
| K3-073-5B | 150.1 | 424.1 | 2.85 | 2.05 | 71.82 | 92.14 | 0.293 | 66.3 |
| K4-091-5A | 106.1 | 288.1 | 2.90 | 2.05 | 63.09 | 85.39 | 0.221 | 50.0 |
| K4-091-5B | 105.1 | 289.1 | 2.90 | 2.05 | 63.04 | 82.94 | 0.211 | 55.0 |
| K3-048-5A | 78.1 | 217.1 | 2.95 | 2.12 | 59.87 | 79.22 | 0.224 | 36.3 |
| K3-047-5A | 88.1 | 243.1 | 2.85 | 2.10 | 64.04 | 81.27 | 0.256 | 58.8 |
| K1-027-5B | 48.1 | 146.1 | 2.90 | 2.05 | 48.68 | 64.67 | 0.208 | 64.4 |

Although not specifically shown in Table 2, above, the weights of the samples tested were also measured and recorded. Strength to weight ratios were found to exceed a ratio of 1.4 to 1 in each of the five Although not specifically shown in Table 2, above, the weights of the samples tested were also measured and recorded. Strength to weight ratios were found to exceed a ratio of 1.4 to 1 in each of the five layer samples except for sample K1-027-5B in which the strength to weight ratio was about 1 to 1. In substantially all cases the strength to weight ratio was at least about or exceeding 1.5 to 1, and in the case of several samples exceeded 2 to 1 and in some cases exceeded 2.5 to 1.

EXAMPLE 2

Figure 7:
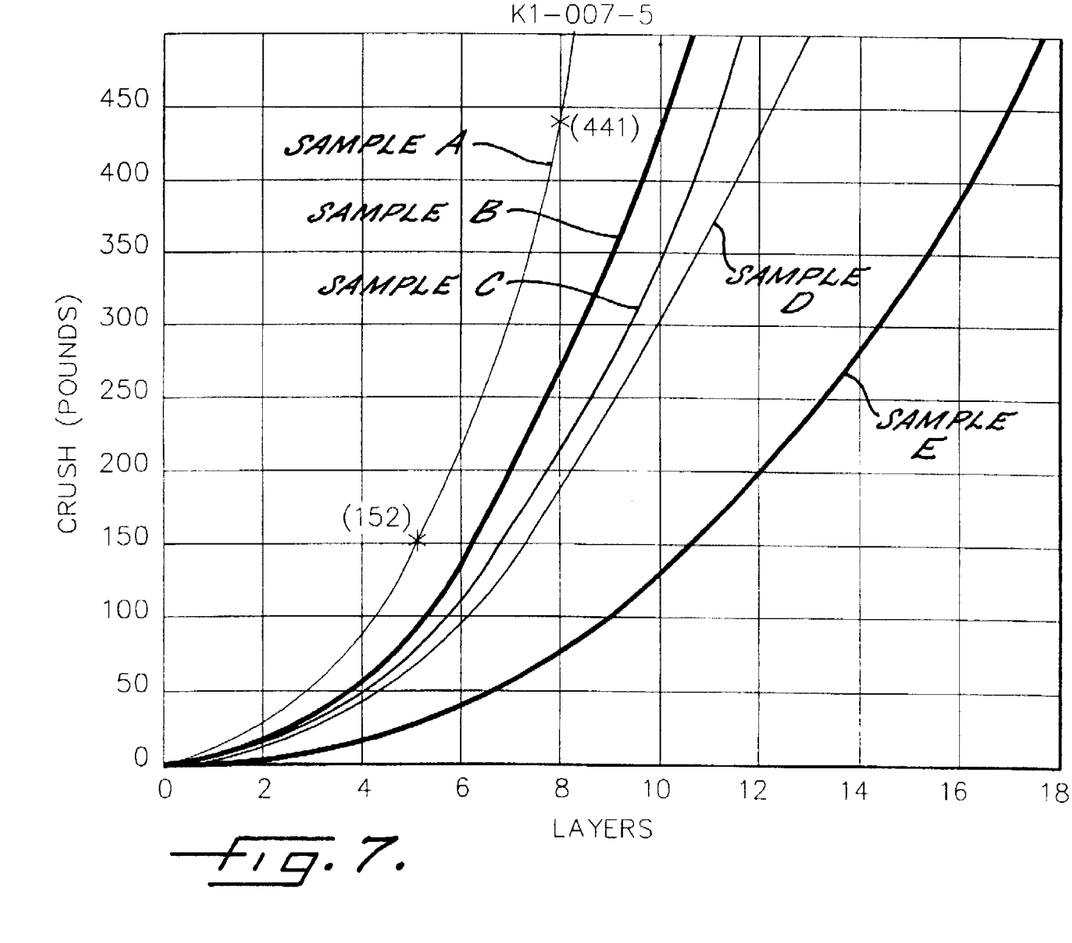
FIG. 7 is a graph comparing cast crush strength in pounds relative to the number of layers used to form the cast, for orthopedic casts according to the present invention and for commercially available glass fiber and synthetic fiber orthopedic casts.

In this Example, a sample orthopedic casting tape of the invention was prepared with a three inch width and the identical construction of Samples K3-077-5A and K3-077-5B in Example 1, above. Cast samples of both five and eight layers were prepared from this sample and evaluated the same as in Example 1, above. The crush strengths thus obtained were compared to casts made and tested in the same manner from samples of three inch width commercially available glass fiber (Samples B, C & D) and synthetic fiber (Sample E) casting tapes identified in Table 3 below.

both glass and synthetic fiber casts. The above results are also presented graphically in FIG. 7. As can be seen, the crush strength of the cast of the present invention exceeded that of commercially available glass and synthetic fiber orthopedic casts of both five and eight layers.

The invention has been described in considerable detail with reference to its preferred embodiments. However many changes and modifications can be made without departing from the spirit and scope of the invention as described in the foregoing detailed description and associated drawings and defined in the following claims.

That which is claimed:

1. An orthopedic casting tape comprising:

an open mesh fibrous tape and a hardenable liquid resin coated onto said fibrous tape, said fibrous tape being a fibrous knit tape comprising primarily unbulked continuous polymeric filaments and being defined by a plurality of wales extending substantially longitudinally along the fibrous tape, at least a portion of the wales comprising an elastic filamentary material in an amount sufficient that said fibrous tape has a longitudinal extensibility of greater than about 5 percent before coating with said resin, said fibrous tape further comprising a plurality of courses extending generally transverse to said plurality of wales, said courses being

TABLE 3

| SAMPLE | | FABRIC | % WT | 24 HR 5 | SAMPLE | 24 HR 8 | WEIGHT |
|---|---|---|---|---|---|---|---|
| A | INVENTION | Knit Polyester & Elastic* | 52 | 152 | 69.7 | 441 | 116 |
| B | Delta-lite ®"S"** | Knit Glass Fiber | 43 | 92.10 | 40.27 | 267.93 | 66.53 |
| C | ScotchCast ®"2"+ | Knit Glass Fiber | 42 | 78.86 | 42.06 | 216.29 | 68.36 |
| D | ScotchCast ®Plus+ | Knit Glass Fiber | 42 | 70.12 | 43.77 | 189.08 | 70.15 |
| E | Delta-Cast ®"C"** | Knit Polyester Tex/Flat & Elastic** | 60 | 27.00 | 33.80 | 80.89 | 54.73 |

*Same construction and yarns as K3-007-5A & B of Example 1
**Same construction and yarns as K12-344-4 of Example 1
**Johnson & Johnson Professional, Inc.
+Minnesota Mining and Manufacturing Co.

As can be seen from Table 2, the strength-to-weight ratio for the cast of the invention exceeded the strength-to weight ratios for the commercially available casting tapes including present in said fibrous tape in an amount of at least 15 courses per inch in a relaxed state, and said wales being present in an amount sufficient such that said casting tapes has at least about 325 openings per square inch in a relaxed state.

2. An orthopedic casting tape as set forth in claim 1 wherein said tape is capable forming a hardened plastic cast having a five layer crush strength of at least about fifteen pounds per inch of tape width, when cured for twenty four hours.

3. An orthopedic casting tape as set forth in claim 1 wherein said knit tape comprises a mesh size of at least about 350 openings per in a relaxed state.

4. An orthopedic casting tape as set forth in claim 1 wherein said elastic filamentary material is substantially inert to said liquid resin.

5. An orthopedic casting tape as set forth in claim 4 wherein said elastomeric filamentary material comprises a dynamically vulcanized blend of olefin rubber and thermoplastic olefin resin.

6. An orthopedic casting tape as set forth in claim 1 wherein said knit tape is a Raschel warp knit fabric.

7. An orthopedic casting tape as set forth in claim 1 wherein said knit tape is a 3 bar Raschel knit and said elastomeric filamentary material is located in bar 3 of the Raschel knit pattern.

8. An orthopedic casting tape as set forth in claim 1 wherein said knit tape is a Raschel knit and in which said elastomeric filamentary material is included in the chain stitch of said fabric.

9. An orthopedic casting tape as set forth in claim 1 wherein said unbulked continuous polymeric filaments comprise multifilament yarns having an average denier of at least about 150.

10. An orthopedic casting tape as set forth in claim 1 wherein said casting tape has an extensibility of greater than about 15 percent in the longitudinal direction.

11. An orthopedic casting tape as set forth in claim 1 wherein said liquid resin comprises a polyurethane prepolymer.

12. An orthopedic casting tape as set forth in claim 1 wherein said unbulked continuous polymeric filaments forming said knit tape are the same or different materials selected from the group consisting of fiber forming polyesters, polyolefins, polyamides, acrylics, and acetates.

13. An orthopedic casting tape as set forth in claim 1 wherein said unbulked continuous polymeric filaments forming said knit tape comprise polyethylene terephthalate.

14. An orthopedic casting tape as set forth in claim 1 wherein said unbulked continuous polymeric filaments forming said knit tape comprise polyethylene terephthalate having a tenacity of less than about 7 grams per denier.

15. An orthopedic casting tape as set forth in claim 1 wherein said tape is capable forming a hardened plastic five layer cast having a strength to weight ratio expressed in (i) crush strength as lbs. load required to achieve a 1 cm. deflection of a 24 hour-cured, five layer, 2.75 inch inside diameter, approximately 3 inch cylinder length test specimen; relative to, (ii) the weight of the same 24 hour cured test specimen in grams, of at least about 1.25 to 1.

16. An orthopedic casting tape as set forth in claim 15 wherein said tape is capable forming a hardened plastic five layer cast having a strength to weight ratio of at least about 1.5 to 1.

17. An orthopedic casting tape comprising:
a knit fibrous, open mesh tape consisting essentially of wales formed of unbulked continuous polyester filaments and elastic filaments and courses formed of unbulked continuous polyester filaments and comprising a mesh size of at least 325 openings per square inch in a relaxed state; and a hardenable liquid resin coated on said open mesh tape said tape being capable of curing to form a hardened plastic cast having a five layer crush strength of at least about twenty pounds per inch of tape width, when cured for twenty hours.

18. An orthopedic casting tape as set forth in claim 17 wherein said knit tape comprises a mesh size of at least 350 openings per square inch.

19. An orthopedic casting tape as set forth in claim 17 wherein said elastic filamentary material is substantially inert to said liquid resin.

20. An orthopedic casting tape as set forth in claim 17 wherein said elastic filamentary material comprises a dynamically vulcanized blend of olefin rubber and thermoplastic olefin resin.

21. An orthopedic casting tape as set forth in claim 17 wherein said knit tape is a Raschel warp knit fabric.

22. An orthopedic casting tape as set forth in claim 17 wherein said knit tape is a 3 bar Raschel knit and said elastic filamentary material is located in bar 3 of said knit tape.

23. An orthopedic casting tape as set forth in claim 17 wherein said knit tape is a Raschel knit and in which said elastic filamentary material is in the chain stitch of said fabric.

24. An orthopedic casting tape as set forth in claim 17 wherein said continuous polymeric filaments comprise a denier of at least about 150.

25. An orthopedic casting tape as set forth in claim 17 wherein said liquid resin comprises a polyurethane prepolymer.

26. An orthopedic casting tape as set forth in claim 17 wherein said knit tape comprises a mesh size of at least 300 openings per square inch in a relaxed state.

27. An orthopedic casting tape as set forth in claim 26 wherein said unbulked continuous polyester filaments forming said knit tape comprise polyethylene terephthalate.

28. An orthopedic casting tape as set forth in claim 27 wherein said unbulked continuous polyester filaments forming said knit tape comprise polyethylene terephthalate having a tenacity of less than about 7 grams per denier.

29. An orthopedic casting tape as set forth in claim 28 wherein said tape is capable forming a hardened plastic five layer cast having a strength to weight ratio expressed in (i) crush strength as lbs. load required to achieve a 1 cm. deflection of a 24 hour-cured, five layer, 2.75 inch inside diameter, approximately 3 inch cylinder length test specimen; relative to, (ii) the weight of the same 24 hour cured test specimen in grams, of at least about 1.25 to 1.

30. An orthopedic casting tape as set forth in claim 29 wherein said tape is capable forming a hardened plastic five layer cast having a strength to weight ratio of at least about 1.5 to 1.

31. An orthopedic cast comprising:
a knit fibrous, open mesh tape constructed essentially of unbulked continuous polyester filaments and elastic filaments, said knit tape having a mesh size of at least 325 openings per square inch; and
a hardenable liquid resin coated on said open mesh tape and being capable of curing to form a hardened plastic cast having a five layer crush strength of at least about 15 pounds per inch of tape width when cured for twenty four hours.

32. An orthopedic splint comprising:
a knit fibrous, open mesh tape constructed essentially of unbulked continuous polyester filaments and elastic filaments, said knit tape having a mesh size of at least 325 openings per square inch; and
a hardenable liquid resin coated on said open mesh tape and being capable of curing to form a hardened plastic splint.

33. A method of producing an orthopedic support material, comprising the steps:

knitting unbulked continuous polymeric filaments into a plurality of wales and a plurality of courses extending generally transverse to said plurality of wales, so as to form a fibrous tape, said courses being present in said fibrous tape in an amount of at least 15 courses per inch in a relaxed state and said wales being present in an amount sufficient to provide a knit fabric tape having at least 325 openings per square inch in a relaxed state;

knitting an elastomeric filamentary material into at least a portion of said wales in an amount sufficient to provide a knit fabric tape having a longitudinal extensibility of greater than 5 percent;

impregnating said fibrous tape with a hardenable liquid resin capable of curing said fibrous tape to form a hardened plastic orthopedic support; and packaging said fibrous tape into a sealed container.

* * * * *

UNITED STATES PATENT AND TRADEMARK OFFICE
CERTIFICATE OF CORRECTION

PATENT NO. : 5,725,487
DATED : March 10, 1998
INVENTOR(S) : Freeman et al.

It is certified that error appears in the above-identified patent and that said Letters Patent is hereby corrected as shown below:

Column 17, line 10, after "per" insert --square inch--.

Column 18, line 8, after "inch" insert --in a relaxed state--.

Column 18, line 33, delete "in a relaxed state".

Signed and Sealed this

Thirtieth Day of June, 1998

Attest:

BRUCE LEHMAN

Attesting Officer    Commissioner of Patents and Trademarks